United States Patent [19]

Schaldach

[11] Patent Number: 5,350,408
[45] Date of Patent: Sep. 27, 1994

[54] CARDIAC PACEMAKER

[75] Inventor: Max Schaldach, Erlangen, Fed. Rep. of Germany

[73] Assignee: Biotronik Mess- und Therapiegerate GmbH & Co. Ingenieurburo Berlin, Berlin, Fed. Rep. of Germany

[21] Appl. No.: 859,449

[22] PCT Filed: Nov. 29, 1990

[86] PCT No.: PCT/DE90/00928
§ 371 Date: May 29, 1992
§ 102(e) Date: May 29, 1992

[87] PCT Pub. No.: WO91/08019
PCT Pub. Date: Jun. 13, 1991

[30] Foreign Application Priority Data

Nov. 29, 1989 [DE] Fed. Rep. of Germany ....... 3939899

[51] Int. Cl.$^5$ ............................................. A61N 1/00
[52] U.S. Cl. ............................................. 607/17
[58] Field of Search ............... 128/419 PG; 607/17-19

[56] References Cited

U.S. PATENT DOCUMENTS

| | | |
|---|---|---|
| 4,381,552 | 4/1983 | Nocilini et al. |
| 4,846,195 | 7/1989 | Alt .................... 128/419 PG |
| 4,856,522 | 8/1989 | Hansen ............... 128/419 PG |
| 4,860,751 | 8/1989 | Callaghan .......... 128/419 PG |
| 4,865,036 | 9/1989 | Chirife. |
| 4,869,251 | 9/1989 | Lekholm et al. ... 128/419 PG |
| 5,010,893 | 4/1991 | Sholder ............... 128/419 PG |
| 5,040,536 | 8/1991 | Riff .................... 128/419 PG |

FOREIGN PATENT DOCUMENTS

| | | |
|---|---|---|
| 0392800 | 10/1990 | European Pat. Off. |
| 3709022 | 9/1988 | Fed. Rep. of Germany. |
| 3709073 | 9/1988 | Fed. Rep. of Germany. |
| 8203780 | 11/1982 | PCT Int'l Appl. |

OTHER PUBLICATIONS

Biomed. Technik 34(1989), 191–196, "Motion Energy as a Control Variable for Sensor-Driven Rate Adaptation," M. Hubmann et al.

Primary Examiner—Lee S. Cohen
Assistant Examiner—Marianne Parker
Attorney, Agent, or Firm—Spencer, Frank & Schneider

[57] ABSTRACT

A controlled-rate, artificial cardiac pacemaker (14) comprises a module (12) for adapting the stimulation rate to the patient's actual physical load. In the case of limited or non-existent activity, the output signal of a sensor (10, 11) for the patient's activity status constitutes a control signal for a circuit (20) which reduces the energy supplied to the module for adapting the stimulation rate of the artificial cardiac pacemaker to the patient's actual physical load.

13 Claims, 2 Drawing Sheets

CARDIAC PACEMAKER

BACKGROUND OF THE INVENTION

1. Field of the Invention

The invention relates to a rate controlled cardiac pacemaker including a component group to adapt a stimulation rate to a patient's momentary physical stress.

2. Background Information

The publication "Biomedizinische Technik (Biomedical Technology), 34 (1989), pages 191-196" discloses a cardiac pacemaker developed for rate-adaptive single and dual chamber stimulation whose rate control is effected on the basis of measuring the low frequency oscillation spectrum as signals characterizing the patient's activity. For this purpose, the signals are limited in level, are amplified in a frequency selective manner and their spectral component is evaluated for the physical stress.

With the aid of a piezoelectric transducer integrated in the pacemaker housing and with a subsequently connected signal processing circuit, the motion values generated by physical stress can be detected and the pacemaker can be optimally physiologically adapted to the patient's given stress state.

However, the signal processing unit connected to the output of the piezoelectric transducer that is integrated in the pacemaker housing requires additional current beyond that required by the other circuit components of the pacemaker.

SUMMARY OF THE INVENTION

It is the object of the invention to provide a cardiac pacemaker which reduces the energy requirement for the pacemaker when the physical activity of the patient is reduced.

This is accomplished in a cardiac pacemaker as defined in the preamble of claim 1 by the features defined in its characterizing portion.

The invention is based on the realization that with reduced activity the components for detecting and adapting the heart rate to this activity can also be operated with reduced energy since the initiation of changes in the heart rate is not required or only very rarely.

The detection of the patient's activity can here be effected either by a sensor that is separate from the sensor for determining physical stress for controlling the heart rate as, for example, by a position sensor for determining the patient's position in space (recumbent or standing) or by the sensor for physical stress itself. In that case, the average frequency of the determination of the momentary stress is preferably raised with the stress so that the adaptation is slower during rest phases.

The component for changing the heart rate may possibly be switched off completely during a rest phase. If the heart rate is determined by way of a sensor for determining the performance capability of the patient, which sensor is separated from the activity sensor, this sensor may also be switched off during a rest phase. In the other case, regular temporary switching in at relatively great time intervals is sufficient.

To determine the rest phase of a patient, a circuit may also be utilized which determines the periodicity of the regular rest phases of the patient and derives a control signal therefrom that causes the energy consumption of the component influencing the pacemaker stimulation rate to be reduced. If necessary, the repetition rate of the temporary switching in of the means for detecting activity may then also be reduced during the regular rest phases.

Other modifications and advantageous features of the invention are defined in the claims, the description below and in the drawings.

In order to prevent the relatively current intensive evaluation program of the subsequently connected signal processing circuit of an activity sensor system from being activated without interruption, a circuit is preferably employed which detects the periodic rhythm of the patient's activity and rest phases and switches the energy supply of the circuit for the activity dependent control of the heart rate to its highest value only during the activity phases. Preferably, this results in an adaptation to a day/night rhythm (activity and rest phases) for the patient with respect to the connection of the activity sensor system during the patient's day phase and its disconnection during the night phase, respectively.

If a single activity sensor system is employed for controlling the reduction of the energy supply as well as the rate control, it is favorable to increase the frequency of activation of the circuit for the detection of activity (and thus the energy consumption) in times of increased activity (activity phase) or to reduce its response level, respectively, while in times of lower activity (rest phase) the number of activations of the circuit per unit time is reduced (and thus also the energy consumption). The cyclic control as a function of the regular activity and rest phases of a patient in a 24-hour rhythm utilizes this "activity dependent activity" control of the activity detection circuit only during the patient's averaged rest phases.

The solution according to the invention ensures in an advantageous manner that the circuit means for detecting activity are supplied with increased energy only if the patient is in an activity phase where rapid adaptation of the heart stimulation rate to changes in stress is necessary. Individual movements, as they occur, for example, during the sleep phase, will thus not cause the cardiac pacemaker to be switched to an increased stimulation rate.

A solution is proposed as advantageous which adapts itself to the changing day/night rhythms of the patient as they occur, for example, upon a change from summer to winter or during air travel connected with different time zones as well as to a day/night ratio other than one. For this purpose, a phase sequential system is employed in particular such as, for example, a PLL [phase locked loop] system with its adaptability to the frequency and phase position of changing reference signals. The reference phase position here is, for example, the transition from the activity to the rest phase, with the length of the rest phase then being retained in an integrating memory for average time values.

In another advantageous solution, an event counter is employed which retains signals characteristic of the activity phases in the momentarily addressed memory location of an average value memory that is cyclically addressable in a 24-hour rhythm. The number of activity events picked up, on the average, in earlier 24-hour cycles is read out simultaneously. Those memory locations which, on the average, store a number of activity events that exceeds a predetermined minimum value, when read out at a momentary point in time, then generate a signal indicating an activity state.

In this way, the pacemaker is given a sort of "internal clock" which enables it to adapt its own activity to that of the patient. Thus, in particular, the repetition rate of measurements or calculations that are performed only at time intervals in order to save energy is further reduced during the patient's rest phase.

In particular, the operation of a circuit for adapting the number of measurements or calculations performed by the processor to the momentary activity of the patient, can be limited to the patient's rest phases. In this way, the heart rate is adapted relatively quickly to physical stress during the regular activity phase (that is, usually during the day) while during the night phase, during which changes in stress are generally not expected, the adaptation is slower. This, however, corresponds entirely to the behavior of the patient himself who in such a case will also react rather "sleepily". Only if the patient develops an activity phase regularly at certain (initially unusual) times, will the system adapt itself to this regularity due to its time adaptability (learning capability).

To detect the day/night rhythm and also other arbitrary changes between activity and rest phases for the patient, a sensor system may be employed, in particular, which monitors the patient's activities and switches on the heart rate control upon detection.

BRIEF DESCRIPTION OF THE DRAWINGS

Advantageous features of the invention are defined in the dependent claims and will be described in greater detail below together with a description of the preferred embodiment of the invention and reference to the drawing figures in which:

DETAILED DESCRIPTION OF THE PREFERRED EMBODIMENTS

Figure 1:
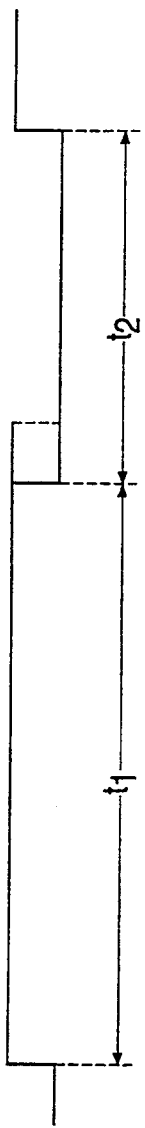
FIG. 1 is a diagram of the time sequence of a patient's activity in a 24-hour rhythm.

In FIG. 1, a diagram serves to initially illustrate the change between the various activity phases of the patient. The figure shows the day/night activity of a patient with t1 as the active period and t2 as the rest period. The beginning of the active period t1 may change due to external influences such as summer/winter or different times zones. The pulsing ratio between day and night is also subject to changes. These changes are detected by the so-called "internal clock" of a person.

Figure 2:
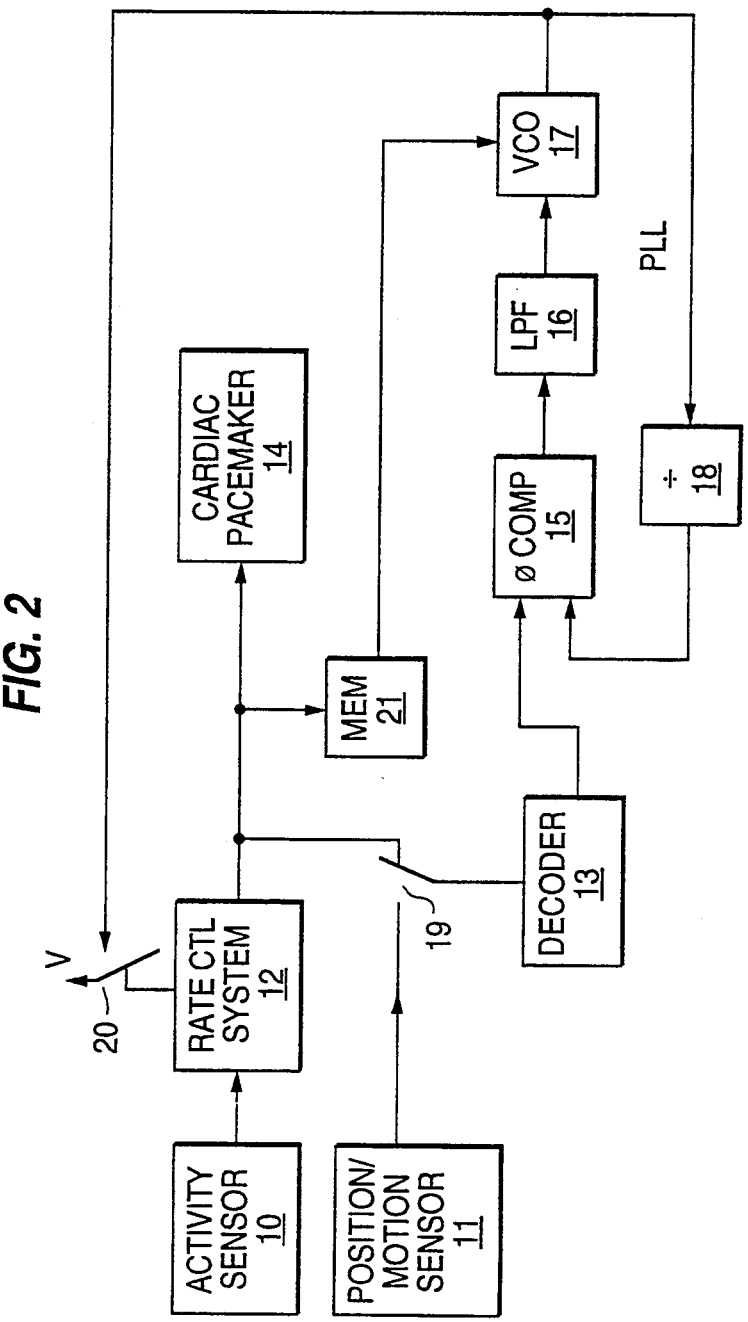
FIG. 2 depicts an evaluation circuit as an embodiment of the invention.

FIG. 2 depicts an evaluation circuit for the changes in day/night activity which derives therefrom a control signal for switching off a rate control system 12 in order to conserve energy. The activity criterion may be derived from an activity sensor 10 in rate control system 12. The rate control system may be any system that causes the pacemaker rate to follow the patient's momentary stress, for example, a sensor for detecting the systolic intervals, an activity evaluation system or a system for converting the patient's determined respiration rate to a value representative of the patient's momentary stress. The output of rate control system 12 is connected to a cardiac pacemaker 14 which performs an optimum pacemaker function in dependence on the patient's stress.

From the output signal of the rate control system 12, a decoder 13 obtains a reference frequency for a PLL circuit. Decoder 13 generates a voltage curve for the reference frequency which corresponds to FIG. 1.

A switch 19 can also be employed to derive the reference frequency from a position sensor 11 or a motion sensor. The reference frequency is then fed to a phase comparison circuit 15. As the second frequency, phase comparison circuit 15 receives the output signal of a voltage controlled oscillator 17 by way of a divider 18. The output signal of phase comparison circuit 15 is conducted through a lowpass filter 16 to the voltage controlled oscillator 17. The output signal of voltage controlled oscillator 17 is employed, if required by way of a divider (not shown), as the control signal for a controllable switch 20 which during the day phase connects the activity sensor system 12 to the supply voltage V and during the night phase disconnects this supply.

Instead of being disconnected completely, switch 20 may also be switched in periodically at a reduced repetition rate in order to save energy in this way.

Since the pulsing ratio between day and night may be different in a patient, the invention additionally provides an integrating memory 21 which generates a voltage value that is proportional to the pulsing ratio. This voltage value is preferably employed to adapt the pulsing ratio of the frequency of the voltage controlled oscillator 17 to the pulsing ratio between day and night.

A PLL circuit is employed in this connection which includes a voltage controlled oscillator 17 operating at a low frequency. In this way, the periodicity of the moment of awakening in the morning is predicted correctly with great probability. The PLL system detects the phase position of the daily rise or drop in physical activity at the end or beginning of the daily rest phase and sets the pacemaker activity accordingly. This requires merely a matching of phase positions since the 24-hour repetition rate is determined by the revolution of the earth around the sun—and thus the natural day/night rhythm—and is fixed for all patients. However, phase shifts to be compensated result, for example, from air travel (jet lag). The above-described circuit need not be set like a clock since its 24-hour frequency also adapts itself to the daily rhythm of the patient so that no highly accurate timer is required.

In another embodiment of the invention, component groups 15 to 18 and 21 are replaced by a memory that is cyclically addressed in a 24-hour rhythm and has a memory location for each one of a number of time intervals. The momentary activity events are added to the stored average value for the momentarily addressed time interval for averaging, while the memory contents in the memory location associated with the previous reaching of the respective time interval is read out and the output signal actuates a switch V, that is, the switch closes for a stored value indicative of increased activity or closes at a higher repetition rate while for a memory content belonging to a lower activity, switch 20 is opened or closed at a lower frequency, respectively, in order to prevent the energy supply of the pacemaker from being exhausted prematurely.

In this way, the pacemaker detects the patient's biorhythm and adapts the stimulation behavior accordingly like an "internal clock" without requiring additional measuring value pickups for this purpose.

Figure 3:
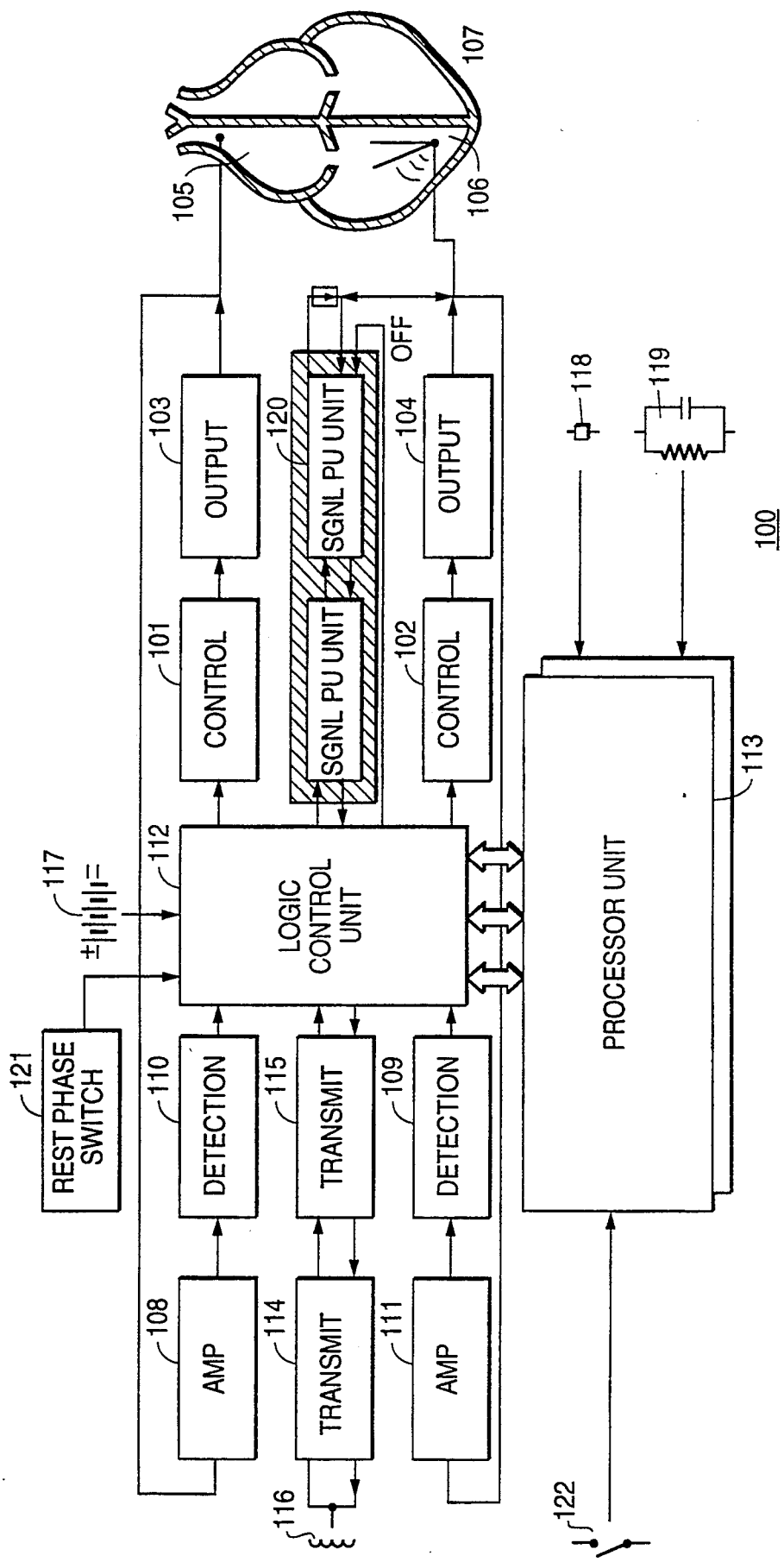
FIG. 3 is a block circuit diagram for a rate-controlled cardiac pacemaker equipped with the measures according to the invention.

FIG. 3 is a block circuit diagram for a rate controlled cardiac pacemaker 100. This cardiac pacemaker stimulates by way of control stages 101 and 102, respectively, and output stages 103 and 104, respectively, the atrium 105 and the ventricle 106, respectively of the heart 107 by means of appropriate electrodes that are connected to the output circuits. These electrodes also pick up from the heart signals characteristic for the action of the heart itself and feed these to an input amplifier circuit 108 and 111, respectively. These signals are processed by way of subsequently connected detection stages 110 and 109, respectively—in each case separately for atrium and ventricle.

These data are conducted to a processor unit 113 by way of logic control unit 112. This processor unit 113 is connected with the logic control unit 112 by way of a data bus, a control bus and an additional bus so that the digitized signals picked up in the atrium and ventricle can be read out from the processor unit and additional digital control signals can be put out to generate stimulation pulses in the atrium and ventricle. Logic control unit 112 has the same relationship to processor unit-113 as a control unit for a peripheral unit, for example, an interface equipped with an A/D-D/A converter for picking up and putting out external analog signals, often also called an input-output unit.

Also connected with the logic control unit is a bidirectional transmission channel 114, 115 which is able to transmit by means of an inductance 116 signals picked up from the heart to outside of the patient, and also control signals for programming the cardiac pacemaker from outside the patient to the pacemaker. Further provided is a battery 117 for supplying the entire pacemaker, a quartz crystal 118 and a resonant circuit 119 as timer or reserve timer, respectively.

A signal pickup unit 120 serves to determine a physiological parameter which constitutes a measure for physical stress within the patient's body. In the illustrated embodiment this unit is a pulse generator for putting out measurement pulses (current pulses i) in the right ventricle from which can be determined by way of the electrode disposed in the ventricle the momentary electrical resistance within the ventricle at predetermined times. Circuit 120 further includes a line for disconnecting this module so that the emission of current pulses, in particular, is prevented. Logic control unit 112 is able to disconnect block 120 by means of an "off" signal. This disconnection is effected by processor unit 113.

Finally, a rest phase switch 121 is shown which detects phases of physical activity and rest in the patient. The rest phase switch is connected with logic control unit 112 for direct data exchange. Rest phase switch 121 includes the PLL unit described above which includes a position or motion sensor. This unit is configured in such a way that the output signal of the position or motion sensor is linked by means of AND gates with the output signal of the unit detecting the patient's activity rhythm. Sporadic movements or changes in the patient's position are detected as the beginning of an activity phase only if the cycle of the expected activity phase has also begun so that the cardiac pacemaker is prevented from beginning an operating mode associated with the patient's active phase (daytime program) already upon individual changes in position, for example during sleep. Only if the system detects more intensive activity of the patient outside of a phase in which a rest phase would actually be expected, will the pacemaker also switch to its program associated with the active phase. In this program, for example, block 121 is activated by suppression of the "off" signal so that the stimulation rate is change adequately for physical stress.

Since this circuit consumes a considerable amount of battery energy because of its regularly generated current pulses, its use can be dispensed with during the patient's rest phases. The arrangement according to the invention ensures that activation takes place only if movements or changes in the patient's position actually belong to a longer-lasting activity.

By means of a reed switch 122 and an external magnet, processor unit 113 can be put into a predetermined state in which stimulation is effected preferably at a fixed rate.

The invention is not limited in its embodiments to the above-described preferred embodiment. Rather, a number of variations are conceivable which take advantage of the described solution even for basically different configurations.

I claim:

1. An apparatus for use with a cardiac pacemaker having a stimulation rate, the apparatus comprising:
   means for adapting the stimulation rate of the cardiac pacemaker to momentary physical stress of a patient, said means for adapting the stimulation rate of the cardiac pacemaker to the momentary physical stress of the patient being supplied with energy;
   means for reducing the energy supplied to said means for adapting the stimulation rate of the cardiac pacemaker to the momentary physical stress of the patient; and
   means for determining activity of the patient; wherein when the patient is inactive or when patient activity is reduced, said means for determining activity of the patient provides an output signal to said means for reducing energy supplied to said means for adapting, the output signal controlling the means for reducing energy to reduce the energy supplied to said means for adapting;
   wherein the means for determining the activity of the patient outputs the output signal if a predetermined minimum activity level is not reached for a predetermined minimum period of time, and if a sum of a number of the minimum periods of time within a predetermined time interval exceeds a predetermined value.

2. An apparatus according to claim 1, wherein the circuit for determining the activity of the patient comprises a sensor for sensing oscillations characteristic of the activity of the patient.

3. An apparatus according to claim 1, wherein the circuit for determining the activity of the patient comprises a motion sensor.

4. An apparatus for use with a cardiac pacemaker having a stimulation rate, the apparatus comprising:
   means for adapting the stimulation rate of the cardiac pacemaker to momentary physical stress of a patient, said means for adapting the stimulation rate of the cardiac pacemaker to the momentary physical stress of the patient being supplied with energy;
   means for reducing the energy supplied to said means for adapting the stimulation rate of the cardiac pacemaker to the momentary physical stress of the patient; and
   means for determining activity of the patient, coupled to said circuit for reducing energy supplied to said means for adapting, wherein when the patient is inactive or when patient activity is reduced, said means for determining activity of the patient provides an output signal to said means for reducing energy supplied to said means for adapting, the output signal controlling the means for reducing energy to reduce the energy supplied to said means for adapting;

wherein the means for detecting the activity of the patient comprises a position sensor for discriminating between a recumbent and a standing position of the patient.

5. An apparatus for use with a cardiac pacemaker having a stimulation rate, the apparatus comprising:

means for adapting the stimulation rate of the cardiac pacemaker to momentary physical stress of a patient, said means for adapting the stimulation rate of the cardiac pacemaker to the momentary physical stress of the patient being supplied with energy;

means for reducing the energy supplied to said means for adapting the stimulation rate of the cardiac pacemaker to the momentary physical stress of the patient; and means for determining activity of the patient, wherein, when the patient is inactive or when patient activity is reduced, said means for determining activity of the patient provides an output signal to said means for reducing energy supplied to said means for adapting, the output signal controlling the means for reducing energy to reduce the energy supplied to said means for adapting;

wherein the means for determining the activity of the patient comprises:

a sensor having an output for sensing the activity of the patient;

a rate control circuit having an input connected with the output of said sensor and timer means, coupled to said sensor by said rate control circuit, for generating a signal indicating a rest phase or an activity phase based upon the changes in said rest and activity phase as indicated by changes of the sensor output picked up during a preceding time period, synchronized in a 24-hour rhythm with activity and rest phases that occur in continuous alternation;

wherein said sensor, when the patient is inactive, when patient activity is low over a period of time, or when patient activity exceeds a predetermined level, respectively, emits a synchronization input signal for said timer means.

6. An apparatus according to claim 5, wherein said timer means comprises one of a phase locked loop circuit and an event counter;

wherein the output signal of the sensor provides one of a reference frequency signal to the phase locked loop circuit or an event signal to be retained in said event counter which periodically, in a 24-hour cycle, addresses memory locations for event signals thereby providing time dependent control than can be synchronized in a 24-hour rhythm.

7. An apparatus according to claim 6, wherein the phase locked loop means includes a voltage controlled oscillator operating at a low frequency that lies in a range of a frequency of an activity/rest rhythm.

8. An apparatus for use with a cardiac pacemaker having a stimulation rate, the apparatus comprising:

means for adapting the stimulation rate of the cardiac pacemaker to momentary physical stress of a patient, said means for adapting the stimulation rate of the cardiac pacemaker to the momentary physical stress of the patient being supplied with energy;

means for reducing the energy supplied to said means for adapting the stimulation rate of the cardiac pacemaker to the momentary physical stress of the patient; and means for determining activity of the patient, wherein, when the patient is inactive or when patient activity is reduced, said means for determining activity of the patient provides an output signal to said means for reducing energy supplied to said means for adapting, the output signal controlling the means for reducing energy to reduce the energy supplied to said means for adapting;

wherein the means for reducing the energy supplied comprises a circuit which reduces a number of periodic turn-on cycles of said means for adapting within a predetermined period of time.

9. An apparatus according to claim 8, wherein the means for adapting the stimulation rate to momentary physical stress of the patient has an input for receiving an input signal and wherein the means for determining the activity of the patient further and simultaneously produces an input signal for the means for adapting the stimulation rate to momentary physical stress of the patient; and said apparatus further comprising means for determining an input value for the means for adapting the stimulation rate to momentary physical stress of the patient, an energy supply input of said further sensor also being connected with the means for reducing the energy supplied.

10. An evaluation circuit for detecting changes in patient activity and producing a control signal for switching off energy supplied by a power source to a rate control system for a cardiac pacemaker coincident with a predetermined rest phase or when activity of the patient does not otherwise exceed a predetermined threshold, the evaluation circuit comprising:

an activity sensor means for providing signals to the rate control system;

a position sensor means for providing signals indicative of a patient's position;

a selector switch means coupled to the rate control system, the decoder, and the position sensor for switching signals to the decoder from either the rate control system or the position sensor means;

a decoder means for receive signals from the selector switch means and produce a reference frequency signal output;

a phase locked loop means for receiving the reference frequency signal from the decoder and producing a control signal; and a controllable switch coupled between the rate control system and the power source, the controllable switch being controlled by the control signal from said phase locked loop circuit.

11. The evaluation circuit according to claim 10, further comprising an integrating memory means, coupled to said phase locked lop circuit, for generating a voltage that is proportional to a patient pulsing ratio between day and night and providing the voltage to said phase locked loop circuit to adapt a frequency of said phase locked loop means between day and night values.

12. The evaluation circuit according to claim 10, wherein the phase locked loop means comprises:

phase comparator means, coupled to the decoder, for receiving a first and a second input signal, the first input signal being the reference frequency signal output by the decoder, the second input signal being derived from the control signal produced by the phase locked loop, and providing a comparison signal output;

a low pass filter means coupled for receiving the comparison signal from the phase comparator and producing a filtered output signal;

voltage controlled oscillator means for receiving the filtered output signal from the low pass filter and producing the control signal; and divider means for receiving the control signal from the voltage controlled oscillator and providing the second input signal to the phase comparator.

13. A rate controlled cardiac pacemaker comprising:

output means for stimulating a patient heart with electrical signals through electrodes;

control means for controlling the output means;

amplifier means for receiving and amplifying signals from the patient heart;

detection means for receiving the amplified signals from the amplifying means and providing detection signals;

rest phase switch means for detecting phases of physical activity and rest of a patient and producing activity signals when activity of the patient coincides with a predetermined active phase or when activity of the patient otherwise exceeds a predetermined threshold;

logic control means for receiving the activity signals from said rest phase switch means and the detection signals from said detection means, and providing control signals to said control means; and processor means coupled to said logic control means for receiving signals from said logic control means and for providing said control signals to said logic control means, said logic control means functioning as an interface between said processor means and the other means of said rate controlled cardiac pacemaker.

* * * * *